United States Patent [19]

Nowak et al.

[11] 4,003,865

[45] Jan. 18, 1977

[54] ENZYME INHIBITORS, USES AND COMPOSITIONS CONTAINING SAME

[75] Inventors: Milton Nowak, South Orange; William Singer, Teaneck, both of N.J.

[73] Assignee: Troy Chemical Corporation, Newark, N.J.

[22] Filed: Feb. 2, 1973

[21] Appl. No.: 328,990

[52] U.S. Cl. .................... 260/17 R; 106/15 R; 106/170; 106/176; 106/197 R
[51] Int. Cl.$^2$ .................................. C08L 1/26
[58] Field of Search ........... 106/186, 170, 197 R, 106/15 AF, 176; 252/403; 260/17.4, 17

[56] References Cited

UNITED STATES PATENTS

| | | | |
|---|---|---|---|
| 2,881,143 | 4/1959 | Wilson | 260/17.4 ST |
| 2,976,163 | 3/1961 | Bitting et al. | 106/170 X |
| 2,990,266 | 6/1961 | Eden | 71/121 X |
| 3,100,674 | 8/1963 | Steiger | 8/127.6 |
| 3,255,000 | 6/1966 | Gates | 260/117 |
| 3,269,967 | 8/1966 | Broadhead | 260/22 A |
| 3,652,313 | 3/1972 | Nagata | 106/197 R |
| 3,749,573 | 7/1973 | Froehlich | 96/111 |

FOREIGN PATENTS OR APPLICATIONS

| | | |
|---|---|---|
| 1,903,864 | 8/1970 | Germany |
| 920,301 | 3/1963 | United Kingdom |

*Primary Examiner*—Theodore Morris
*Attorney, Agent, or Firm*—E. Janet Berry; Lawrence Rosen

[57] ABSTRACT

Adducts of formaldehyde and selected amines (primary and secondary) and their use as enzyme inhibitors in aqueous systems containing cellulosic substances and compositions containing same; and particularly aqueous paint compositions containing said adducts as enzyme inhibitors to retard hydrolytic splitting of cellulose linkages.

17 Claims, No Drawings

ENZYME INHIBITORS, USES AND COMPOSITIONS CONTAINING SAME

This invention relates to a novel process and composition for the inhibition of enzyme attack on aqueous mixtures containing cellulosic derivatives as thickeners and/or viscosity improvers, and more particularly, for improvements in aqueous cellulose-containing paint compositions.

One problem that exists in the paint industry is the loss of viscosity of aqueous latex paints that are found to be completely sterile. This phenomenon is attributed to the existence in such aqueous paint systems of the chemical catalysts known generally as enzymes. These enzymes are produced by bacterial and fungal organisms for instance as digestive aids to facilitate use by the organisms of cellulosic derivatives as food. Thus, there is a close relationship between these organisms and the catalysts (enzymes) they produce, and of the purpose for the enzymes themselves.

One theory for their action is that these enzymes are capable of breaking the ether linkage existing between anhydroglucose groups in the cellulosic polymer, thereby reducing the polymer size and causing a loss in viscosity of solutions or dispersions containing them. The ultimate break-down result of such a catalyzed chemical hydrolytic attack is the formation of glucose as the end-product. The end-products resulting from the fragmentation of the cellulosic polymer, would be available as food for micro-organisms, if they were present.

Obviously, these micro-organisms are not present, since the paints involved have been found to be sterile. The inescapable conclusion, therefore, is that the micro-organisms themselves were present at an early stage of manufacture, and produced the enzyme at that time. Therefore, it appears that subsequent treatment of the paints with a preservative killed the micro-organisms, but the enzymes, not being alive, were not attacked, and remained behind with their potency for hydrolytic fragmentation largely unreduced.

A number of substances have been discovered and used in the past for rendering aqueous paint compositions sterile. For example, metal salts, such as salts of mercury, tin, and copper, as well as organic chemical compounds including the chlorinated phenols, mercaptobenzothiazole, zinc, dimethyldithiocarbamate, and the like have been found beneficial for rendering and maintaining paints sterile.

These compounds are practically without effect, however, in stabilizing paints containing enzymes against viscosity losses caused by the enzymes present. A contaminated paint rendered sterile by these compounds will often continue to lose viscosity when additional cellulosic thickener is added to increase viscosity.

Another source of such undesirable hydrolytic enzymes in the sterile aqueous paint may be introduction of various ingredients previously contaminated with enzymes, prior to their addition to the paint. Such materials might or might not be sterile, but in either case, the preservative in the paint would insure that the resulting paint would be sterile. However, the catalytic enzyme would subsequently be present, again since the enzymes are not rendered inactive by materials and/or processes normally used for sterilization.

Still another possible source of such enzymes in the sterile paint result from poor housekeeping in a paint plant. After mixing of a paint composition in a tank, a certain amount of the material always splashes on the upper walls and cover of the tank. Such splashed paint, if not thoroughly cleaned away, will eventually dry and then function as an ideal substrate for attack by fungal organisms. The preservative present in the paint is not generally present at a level high enough to protect such contaminating films from fungal organisms. Generally, such protection requires the presence of high levels of fungicides, and the bactericides generally in use as preservatives are ineffective for this purpose. As a result, the fungal organisms growing on the film, in the moist warm environment of the tank can readily produce the enzymes which later find their way into the paint.

The attack on the cellulosic thickeners included in the paint by the enzymes thus present causes marked and undesirable viscosity losses over a period of time. Thus a can of sterile paint, at the proper application viscosity when packaged, may after a period of time varying between several days to many months, lose viscosity to such a severe extent that it becomes unuseable as well as unsaleable. The problem is particularly difficult because the viscosity loss occurs despite sterility, is progressive, occurs without prior warning, and is largely unpredictable.

It is obvious that prevention of such enzyme initiated viscosity losses for instance by addition of a chemical inhibitor would be very desirable and would offer great commercial advantages.

The adducts of certain selected amines with formaldehyde have been found to be effective inhibitors of enzymatic degradation of water-soluble cellulosic derivatives. These compounds show a marked retarding effect on such enzymatic attack and their degree of protection has proved to be of great value. They are, however, not usually capable of totally preventing viscosity loss in aqueous paints, especially over a prolonged period of time.

Amine-formaldehyde reaction products are themselves very well known but they have not previously been described as inhibitors for enzyme degradation of celluloses. Certain of the adducts are made commercially and are available for other purposes. The ethanolamine-formaldehyde adduct is known for use as a disinfectant for cutting oils (British Pat. No. 920,301) and also for controlling plant growth (U.S. Pat. No. 2,990,266). The compound resulting from reaction of ethylamine and formaldehyde is known by the trade name "Vancide TH" and is the cyclic compound hexahydro-1,3,5-triethyl-s-triazine. It finds use as a preservative.

Although the exact mechanism of the inhibition by the adducts is not known, and it is not intended to limit the scope or effect of the invention by any theoretical considerations, it is believed that the activity of this class of compounds as enzyme inhibitors depends at least in part on the formation and availability of nitrogen bonded methylol groups. These methylol groups are very reactive, and can readily react with susceptible sites in the enzyme molecule. These susceptible groups are probably amide linkages, since the active portions of enzymes are generally considered to be polypeptides or proteins.

The formation of the amine adduct may take place between formaldehyde and either primary or secondary amines as follows:

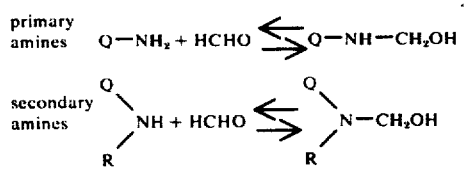

wherein Q and R are alkyl, alkoxy, or substituted alkyl or alkoxy groups and may be saturated or unsaturated. The groups Q and R together should not contain more than approximately ten carbon atoms.

If the amine is a primary one, cyclization is possible as follows:

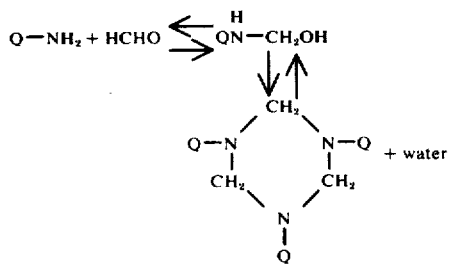

where Q has the same meaning as above.

Etherification is another possible reaction:

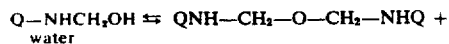

If the amine is a secondary one, etherification is possible:

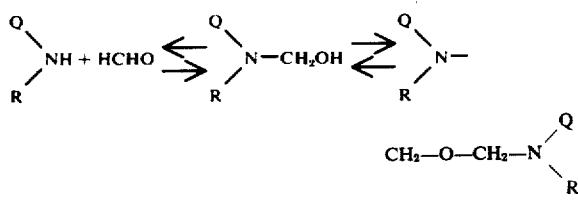

where Q and R have the same meaning as above.

It is probable that all of these reactions may take place to some extent but the activity of any particular adduct compound will depend on the availability of free methylol groups. Since secondary amines can not cyclize, one reaction type is eliminated, and it would be expected that adducts from such compounds would be somewhat more active. In general, tests indicate that this is true. However, steric and other factors complicate the reactivity picture, and any given adduct compound may be more or less active than would be predicted from structural considerations.

As indicated by the smaller arrow of the reaction scheme above, the adduct reaction is reversible. The driving force is towards methylol formation, but some free formaldehyde must be assumed to be always present. Formaldehyde is itself an excellent preservative, and these adducts therefore are generally quite active as such for this reason and especially so when first prepared. However, formaldehyde is relatively impermanent (fugitive) as a preservative. It is volatile, and so reactive that if not lost it will generally be inactivated after a relatively short time by various side reactions.

Thus a further advantage of this series of adduct compounds is that the adducts themselves slowly dissociate into their components and thus act to feed formaldehyde slowly into the system, thereby keeping it sterile for a much longer period of time.

The testing procedure for effectiveness is carried out as follows:

Jars containing sterile cellulosic solutions are innoculated, separately, with aspergillus niger and fusarium sp. They are then loosely capped and allowed to stand at room temperature for two weeks. At the end of this time period, the living organisms present are killed through the addition of formaldehyde solution. The two solutions are mixed to give an aqueous mixture of degraded cellulosic together with the enzymes produced by the two organisms.

Five drops of the above mixture are then added to 100 gram quantities of sterile cellulosic solution containing 0.1 g. of enzyme inhibitors. After 12 days, the viscosities of the samples are measured using Gardner viscosity tubes as standards.

The adducts with formaldehyde may be prepared by reaction of formaldehyde (paraformaldehyde is convenient for use) with the selected amine.

Among the amine adducts which have been prepared are those from ethylamine, propylamine, butylamine, isopropylamine, isobutylamine, ethanolamine, isopropanolamine, allylamine, methoxypropylamine, 2-amino-2-methyl-1-propanol, sec.-butylamine, tert.-butylamine, diglycolamine, diethylamine, dipropylamine, and dibutylamine. It is not intended, however, to limit the invention to the formaldehyde adducts of these particular amines.

The adducts which are viscous liquids are relatively simple to prepare. They may be, for instance, either water soluble or water insoluble. They may be made for example by mixing aqueous formaldehyde in approximately equimolar proportions with the selected amine. After stirring at room temperature up to 60°–75° C., the adduct products are decanted from any aqueous layer present. Addition of sodium or potassium hydroxide or carbonate may be helpful before decantation, since they will tend to "salt out" the product. Alternatively, the anhydrous polymeric form of formaldehyde, paraformaldehyde may be used as reactant. No attempt is made to dehydrate the resulting product, since this would probably result in a reduction of methylol groups from further reaction.

The levels generally used will vary between approximately 0.05 and 1 or 2% and the adducts may be added to the completed formulation, and also if desired to the stored cellulosic solutions.

The following examples of the invention are presented for illustrative purposes only and it is in no way intended to limit the invention thereto.

EXAMPLE I

A solution of hydroxyethylcellulose, a compound frequently used as a thickener in paints, made up in water, at a concentration of approximately 1½%, and having a Gardner viscosity of Z-3 to Z-4 was inoculated with aspergillus niger organism. It was allowed to stand at room temperature, loosely capped, for two weeks. At the end of this period, the cloudy, heavily contaminated, low viscosity liquid was sterilized by the addition of 0.1% of a 37% formaldehyde solution.

Simultaneously, the above procedure was repeated, but using fusarium species as the organism. After sterilization of the two mixtures, they were mixed together, and the composite sterile degraded cellulosic solution, containing the enzymes produced by the two organisms but no live organisms themselves, was used to inoculate fresh sterile cellulosic solution, as detailed in subsequent examples.

EXAMPLE II

The adducts of the following amines were prepared by heating and stirring one mole of the amine with 1.1 moles of paraformaldehyde at 50°–60° C. until the paraformaldehyde dissolved. The solutions were permitted to stand overnight and then decanted from any aqueous lower layer that may have formed:

| a) ethylamine | d) isopropylamine |
|---|---|
| b) propylamine | e) isobutylamine |
| c) butylamine | f) ethanolamine |
| g) isopropanolamine | k) secondary butylamine |
| h) allylamine | l) tert. butylamine |
| i) methoxypropylamine | m) diglycolamine |
| j) 2 amino-2-methyl-1-propanol | n) diethylamine |
| | o) dipropylamine |
| | p) dibutylamine |

The products are slightly viscous, pale yellow liquids. Viscosity, specific gravity, and refractive index may be determined but they tend to be variable. These adducts may also be prepared by slowly adding, with cooling, 1 mole amine to 1.1 moles of formaldehyde as a 37% solution. After stirring for 3 hours, the mixtures are allowed to stand overnight. The product is separated from the bulk of the water by addition of potassium or sodium hydroxide and subsequent decantation.

In addition to the above the adduct of methylamine and formaldehyde was prepared. Since methylamine is a gas and is most easily handled as a commercially available 40% solution, the second procedure was used. In this case, no attempt was made to separate the product. The resulting solution (q) was simply considered to be 38.5% active.

EXAMPLE III

Each of the above amine-formaldehyde adducts was added to fresh 100 g. sterile solutions of 15,000 cps hydroxyethyl cellulose at a level of 0.1%, followed by 5 drops of the mixed enzyme solution, as prepared in Example I above. 5 Drops of the mixed enzyme solution were also added to a sterile control, containing no amine-formaldehyde adduct.

These solutions were allowed to stand 12 days at room temperature. At the end of this time, all the solutions, including the unprotected control (B) were found to be sterile. Viscosities were taken using Gardner viscosity tubes. In the Gardner system, running A5 to Z-10, A-5 has the lowest viscosity, and Z-10 the highest. The results from the test solutions of Example II above are given below. The original viscosity of the samples was Z-3.

| a) Z-2 | g) Y | m) U |
|---|---|---|
| b) Z-3 | h) V | n) Z-3 |
| c) X | i) W | o) Z-3 |
| d) Z-3 | j) Y | p) Z-3 |
| e) Z-3 | k) Z-2 | q) Z-2 |
| f) X | l) Z-3 | control) B |

As can be seen the viscosity of the sterile control dropped to the very low viscosity of "B", while the solutions protected by the enzyme inhibitors of this invention exhibited remarkable consistency. Their viscosities remained close to the original high viscosity of Z-3.

EXAMPLE IV

Examples I, II, and III are repeated, using methyl cellulose in place of hydroxyethyl cellulose. However, since enzymatic degradation of methyl cellulose takes place more slowly than with hydroxyethyl cellulose, observations were taken after 30 days. Observations of viscosity were essentially the same as those in Example III.

EXAMPLE V

A latex paint was prepared from the following ingredients:
  250 g. titanium dioxide pigment
  250 g. calcium carbonate pigment
  100 g. aluminum silicate (talc) pigment
  400 g. polyvinyl acetate copolymer latex/55% solids
  150 g. hydroxyethyl cellulose thickener solution
  1 g. formaldehyde solution/37%

5 Drops of the mixed enzyme solution prepared in Example I were added to 200 g. portions of the above paint, to which were added 0.5 g. each of a number of the amine adducts of Example II. The purpose of this test was to determine if the protection observed with cellulosic solutions would also be observed with paints containing them. The measured viscosities are listed below:

Initial paint sample viscosity = 95 K.U. (Stormer Viscosimeter)

Viscosities of the paint samples taken after one week:

| b) 90 K.U. | n) 95 K.U. |
|---|---|
| d) 95 K.U. | o) 94 K.U. |
| k) 91 K.U. | p) 93 K.U. |
| l) 93 K.U. | Control) 85 K.U. |

It can be seen from the above that the control paint without the amine-formaldehyde adduct lost 10 K.U. in the test period. Those compositions containing the adduct lost no more than 5 K.U., indicating considerable protection. Since relatively high levels of enzymes test agents were used in this accelerated test, these results indicate very considerable activity for the invention compounds tested.

EXAMPLE VI

A paint sample was prepared in accordance with the formulation of Example V, except that it was not sterilized with formaldehyde solution. Instead, the amine-formaldehyde adduct prepared from formaldehyde and 2-amino-2-methyl-1-propanol was added at a level of 0.1%. To this portion of paint was added a mixed bacterial culture of Aerobacteraerogines, *Escherichiei coli*, *Bacillus subtilis*, and *pseudomonas aeruginosa*. A test for sterility 48 hours later indicated that the portion of treated paint was sterile but the control paint not containing the amine adduct was not sterile and was very heavily contaminated. It was also found that the viscosity of the paint containing the adduct was substantially unchanged whereas the viscosity of the control paint sample had been reduced to a point which made it useless for normal paint purposes.

EXAMPLE VII

A set of comparative experiments was carried out in the same way as those described in Example VI above, except that the adduct of formaldehyde and monoethanolamine was used to treat the paint. The results obtained were similar to those of Example VI. The control paint sample was contaminated and suffered severe viscosity loss while the treated sample was sterile and had a viscosity substantially unchanged.

What is claimed is:

1. An aqueous paint composition thickened to a viscosity of between 80 and 100 KU units by having incorporated therein at least one cellulosic thickening agent and stabilized against degradation of viscosity by enzyme action on said cellulosic thickening agent by having additionally incorporated therein approximately 0.05% to 2% based on the aqueous composition of at least one adduct of formaldehyde and an amine selected from the group consisting of primary amines and secondary amines, said adduct having the formula Q—NH—CH$_2$OH if the amine is a primary amine, and QRN—CH$_2$OH if the amine is a secondary amine and wherein Q and R are selected from the group consisting of alkyl, alkoxy, substituted alkyl and substituted alkoxy groups and Q and R having no more than a total of ten carbon atoms.

2. The composition of claim 1 in which the amine of the adduct is a primary amine.

3. The composition of claim 1 in which the amine of the adduct is a secondary amine.

4. The composition of claim 1 in which the adduct is the adduct of formaldehyde and propylamine.

5. The composition of claim 1 in which the adduct is the adduct of formaldehyde and butylamine.

6. The composition of claim 1 in which the adduct is the adduct of formaldehyde and isopropylamine.

7. The composition of claim 1 in which the adduct is the adduct of formaldehyde and isobutylamine.

8. The composition of claim 1 in which the adduct is the adduct of formaldehyde and isopropanolamine.

9. The composition of claim 1 in which the adduct is the adduct of formaldehyde and 2 amino-2 -methyl 1 propanol.

10. The composition of claim 1 in which the adduct is the adduct of formaldehyde and diethylamine.

11. The composition of claim 1 in which the adduct is the adduct of formaldehyde and ethanolamine.

12. The composition of claim 1 in which the adduct is the adduct of formaldehyde and dipropylamine.

13. The composition of claim 1 in which the adduct is the adduct of formaldehyde and dibutylamine.

14. An aqueous latex composition thickened to a predetermined viscosity by having incorporated therein a cellulosic thickening agent and stabilized against degradation of viscosity by enzyme action on said cellulosic thickening agent by having additionally incorporated therein approximately 0.05% to 2% based on the aqueous composition of at least one adduct of formaldehyde and an amine selected from the group consisting of primary amines and secondary amines, said adduct having the formula Q—NH—CH$_2$OH if the amine is a primary amine, and QRN—CH$_2$OH if the amine is a secondary amine and wherein Q and R are selected from the group consisting of alkyl, alkoxy, substituted alkyl and substituted alkoxy groups and Q and R having no more than a total of ten carbon atoms.

15. A method for inhibiting enzyme activity resulting in decreased viscosity of aqueous paint compositions containing at least one cellulosic thickener, said decreased viscosity being caused by enzyme action on said cellulosic thickener, which comprises adding to an aqueous paint composition from approximately 0.05% to 2% based on the aqueous composition of at least one adduct of formaldehyde and an amine selected from the group consisting of primary amines and secondary amines, said adduct having the formula Q—NH—CH$_2$OH if the amine is a primary amine, and QRN—CH$_2$OH if the amine is a secondary amine and wherein Q and R are selected from the group consisting of alkyl, alkoxy, substituted alkyl and substituted alkoxy groups and Q and R having no more than a total of ten carbon atoms.

16. The method of claim 1 in which said adduct is formaldehyde and a primary amine.

17. The method of claim 1 in which said adduct is formaldehyde and a secondary amine.

* * * * *

Disclaimer 4,003,865.—*Milton Nowak*, South Orange and *William Singer*, Teaneck, N.J. ENZYME INHIBITORS, USES AND COMPOSITIONS CONTAINING SAME. Patent dated Jan. 18, 1977. Disclaimer filed July 6, 1982, by the assignee, *Troy Chemical Corp., Inc.*

Hereby enters this disclaimer to claims 1, 2, 3, 4, 5, 6, 7, 8, 10, 11, 12, 13, 14, 15, 16 and 17 of said patent.

[*Official Gazette October 11, 1983.*]